United States Patent
Dumic et al.

(10) Patent No.: US 7,037,928 B2
(45) Date of Patent: May 2, 2006

(54) COMPOSITIONS OF N-(METHYLETHYLAMINOCARBONYL)-4-(-3-METHYLPHENYLAMINO)-3-PYRIDYLSULFONAMIDE AND CYCLIC OLIGOSACCHARIDES

(75) Inventors: Miljenko Dumic, Zagreb (HR); Darko Filic, Zagreb (HR); Bozena Klepic, Jastrebarsko (HR); Aleksandar Danilovski, Rijeka (HR); Marijan Tudja, Zagreb (HR)

(73) Assignee: PLIVA, farmaceutska industrija, dionicko drustvo, Zagreb (HR)

( * ) Notice: Subject to any disclaimer, the term of this patent is extended or adjusted under 35 U.S.C. 154(b) by 101 days.

(21) Appl. No.: 10/416,303

(22) PCT Filed: Jan. 31, 2001

(86) PCT No.: PCT/HR01/00004

§ 371 (c)(1),
(2), (4) Date: May 9, 2003

(87) PCT Pub. No.: WO02/38186

PCT Pub. Date: May 16, 2002

(65) Prior Publication Data

US 2004/0039204 A1    Feb. 26, 2004

(30) Foreign Application Priority Data

Nov. 10, 2000  (HR) .................. P 20000765 A (51) Int. Cl.
*A61K 31/44* (2006.01)
*C07D 213/02* (2006.01)

(52) U.S. Cl. .............. 514/349; 546/297; 546/309; 514/352

(58) Field of Classification Search .......... 546/309, 546/297; 514/352, 349
See application file for complete search history.

(56) References Cited

U.S. PATENT DOCUMENTS 4,822,807 A * 4/1989 Topfmeier et al. .......... 514/347
6,828,334 B1 * 12/2004 Gidwani et al. ............ 514/338

\* cited by examiner

*Primary Examiner*—Zinna Northington Davis
(74) *Attorney, Agent, or Firm*—Connolly, Bove, Lodge & Hutz, LLP (57) ABSTRACT

The invention relates to compositions of N-(1-methylethylaminocarbonyl)-4-(3-methylphenylamino)-3-pyridylsulfonamide and cyclic oligosaccharides with increased release, to methods for their preparation, to pharmaceutical froms containing them as well as to their use.

15 Claims, 12 Drawing Sheets

Fig. 1: DSC of β-cyclodextrin

Fig. 2: DSC of the modification I of torasemide

Fig. 3: DSC of the physical mixture of the modification I of torasemide and β-cyclodextrin (molar ratio 1:1)

Fig. 4: DSC of the inclusion complex of the modification I of torasemide and β-cyclodextrin (molar ratio 1:1)

Fig. 5: IR spectrum of β-cyclodextrin recorded in KBr

Fig. 6: IR spectrum of the modification I of torasemide recorded in KBr

Fig. 7: IR spectrum of the physical mixture of the modification I of torasemide and β-cyclodextrin (molar ratio 1:1) recorded in KBr Fig. 8: IR spectrum of the inclusion complex of the modification I of torasemide and β-cyclodextrin (molar ratio 1:1) recorded in KBr Fig. 9: X-ray powder pattern of β-cyclodextrin Fig. 10: X-ray powder pattern of the modification I of torasemide Fig. 11: X-ray powder pattern of the physical mixture of the modification I of torasemide and β-cyclodextrin (molar ratio 1:1)

Fig. 12: X-ray powder pattern of the inclusion complex of the modification I of torasemide and β-cyclodextrin (molar ratio 1:1)

COMPOSITIONS OF N-(METHYLETHYLAMINOCARBONYL)-4-(-3-METHYLPHENYLAMINO)-3-PYRIDYLSULFONAMIDE AND CYCLIC OLIGOSACCHARIDES

The present invention relates to compositions of N-(1-methylethylaminocarbonyl)-4-(3-methylphenylamino)-3-pyridylsulfonamide (further in the text referred to by its generic name "torasemide") and cyclic oligosaccharides with increased release, to methods for their preparation, to pharmaceutical forms containing them as well as to their use.

Torasemide is a new potent diuretic in the class of the so-called "loop diuretics", which is described in the Example 71 of DE patent 25 15 025. Structurally, it entirely differs from diuretics of the same class such as furosemide, bumetanide and azosemide. In addition to diuretic properties it also possesses antihypertensive properties.

As a diuretic of Henle's loop it is interesting as an agent for preventing heart damages or heart tissue damages caused by metabolic or ionic abnormalities associated with ischemia, in the treatment of thrombosis, angina pectoris, asthma, hypertension, nephroedema, pulmonary edema, primary and secondary aldosteronism, Batter's syndrome, tumours, glaucoma, decrease of intraocular pressure, acute or chronic bronchitis, in the treatment of cerebral edema caused by trauma, ischemia, concussion of the brain, metastases or epileptic attacks and in the treatment of nasal infections caused by allergens.

It is well known that torasemide can exist in four crystal modifications: polymorph I [*Acta Cryst.* B34, (1978) 1304–1310], polymorph II (*Acta Cryst.* B34, (1978) 2659–2662], polymorph III (PCT/WO 00/20395) and polymorph V (HR Patent Application No. P 20000328A), and in one amorphous modification (HR Patent Application No. P 20000162A).

Modifications of torasemide (polymorphs I–V) are very hydrophobic and practically insoluble in water. Very poor water-solubility and wettability of torasemide represents a problem in the preparation of pharmaceutical preparations with good dissolution and uniform bioavailability.

The problem of increasing the dissolution rate of active substances that are poorly soluble in water covers many areas ranging from phytopharmaceuticals to pesticides and, in general, all those areas where bioactive substances are used.

The dissolution rate is determined by physical-chemical characteristics of the active substance and particularly by its solubility in water. Thus, the dissolution rate of an active substance is the limiting factor in the absorption process and in the therapeutic activity of the substance. Additionally, disintegration products of the active substance formed in pharmaceutical preparations may also cause different side effects. Therefore an increased solubility and stability achieved by the preparation of a suitable formulation results in an increased efficiency of the active substance. In pharmaceutical industry, the increase of the dissolution rate and of the stability of poorly soluble active substances has been solved by various methods e.g. by micronization, by preparing amorphs, clathrates, by chemical modifications, by pH adjustment and very often by preparing solid compositions of the active substance and physiologically suitable additives making possible the desired physical-chemical transformation of the active substance i.e. improving the dissolution rate and the wettability of the active substance. As physiologically suitable additives there are usually used e.g. polyvinylpyrrolidone, carboxymethylcellulose, hydroxypropyl cellulose and, with increasing frequency, cyclodextrins, commercially available cyclic oligosaccharides consisting of 6, 7 and 8 linked glucopyranose units ($\alpha$-, $\beta$- and $\gamma$-cyclodextrins and their derivatives).

Solid compositions active substance/physiologically suitable additive can be prepared by blending, milling, precipitation, evaporation, lyophilization, spray-drying and melting.

Properties of cyclodextrins are well known and have been described in detail in reviews in periodicals [Szejtli J., *Cyclodextrin Technology* (1988) Kluwer Academic Publishers, Dordrecht; Szejtli J., Cyclodextrins in drug formulations: Part I, *Pharm. Techn. Int.* 3 (1991) 15–22; Szejtli J., Cyclodextrins in drug formulations: Part II, *Pharm. Techn. Int.* 3 (3) (1991) 16–24; T. Loftson, Pharmaceutical Application of $\beta$-Cyclodextrin, *Pharm. Techn. Eur.* 11 (1999) 20; W. Saenger, Cyclodextrin Inclusion Compounds in Research and Industry, *Angew. Chem. Int. Ed. Engl.* 19 (1980) 344].

Cyclodextrins are characterized by the shape of their molecule in the form of a cylinder. Inside the cylinder there is an intramolecular cavity which is hydrophobic, whereas the outer side is hydrophilic. The hydrophobic character of the intramolecular cavity enables other molecules or parts of molecules known as "guest" molecules to penetrate into the host molecule thereby forming inclusion complexes.

An inclusion complex can be stabilized by numerous forces including also Van der Waals' attracting forces and hydrogen bonds. Inclusion complexing of the corresponding "guest" molecule with cyclodextrins may result in numerous physical-chemical changes in the properties of the "guest" molecule. The melting point is changed, the IR spectrum and X-ray powder pattern of the complex are relatively different from those of the pure "guest" molecule or of a simple (not complexed) mixture of the "host" molecule and the "guest" molecule. By means of cyclodextrin inclusion complex, water-insoluble "guest" molecules become more soluble. In many cases chemically unstable compounds are stabilized by inclusion complexing. The said changes in physical-chemical properties of the "guest" molecule resulting from inclusion complexing with cyclodextrins, represent a proof that the cyclodextrin inclusion complex represent an unique form of the solid state of a "guest" molecule.

Though by the preparation of the solid compositions active substance/physiologically suitable additive an increased dissolution rate has been noticed in a large number of poorly soluble pharmaceutically active substances, this cannot be accepted as a rule. Namely, for each active substance and physiologically suitable additive it has to be established which preparation method, physiologically suitable additive and molar ratio active substance/physiologically suitable additive, solvent, time, temperature of the preparation etc. will give a solid composition making possible the desired dissolution rate of the active substance.

Solid compositions of cyclodextrin with various pharmaceutically interesting active substances have been known from patents as well as from the literature and just a few examples are cited here.

Thus, M. I. La Rotonda et al. compared solid compositions of the non-steroid antiinflammatory drug nimesulide and $\beta$-cyclodextrin (molar ratio 1:1) prepared by physical blending, evaporation, lyophilization, spray-drying and kneading and reported that the dissolution rate depends on physical-chemical properties of each solid composition. In comparison to nimesulide alone, the dissolution of nimesulide from solid compositions was significantly accelerated and the solid compositions obtained by lyophilization and spray-drying showed to be the forms with the fastest dissolution of nimesulide [*S.T.P. Pharma Sci.* 10 (2000) 157].

P. R. Vavia et al. also compared solid compositions of nimesulide with β-cyclodextrin and HP-β-cyclodextrin in a molar ratio 1:1 (physical mixtures and lyophilizates). As stated by the authors, in contrast to physical mixtures, the inclusion complexes prepared by lyophilization increased the dissolution of nimesulide, and particularly by the inclusion complex nimesulide/HP-β-cyclodextrins a significantly higher dissolution was achieved [*Drug Develop. Ind. Pharm.* 25 (1999) 543].

J. R. Mayano et al. prepared, by physical mixing, spray-drying and kneading, solid compositions of the drug oxazepam with ,β-cyclodextrin in molar ratios 1:1 and 1:2, and all solid compositions accelerated the dissolution of oxazepam in comparison to oxazepam alone. In the case of physical mixtures, both molar ratios of oxazepam to β-cyclodextrin showed an equal influence on the dissolution of oxazepam whereas the solid compositions prepared by kneading and spray-drying with the molar ratio 1:2 considerably accelerated the dissolution of oxazepam in comparison to those with the molar ratio 1:1 [*Int. J. Pharm.* 114 (1995) 95].

Further, M. Guyot et al. prepared physical mixtures and inclusion complexes of the drug norfloxacin with β-cyclodextrin and HP-β-cyclodextrin in molar ratios 1:1 and 1:2. Physical mixtures as well as inclusion complexes significantly increased the dissolution in comparison to norfloxacin alone. No influence of molar ratios on dissolution was noticed [*Int. J. Pharm.* 123 (1995) 53]

Besides, M. Pedersen et al. stated that physical mixtures of the antimicotic miconazole and β-cyclodextrin with the molar ratio 1:2 show a faster dissolution in comparison to the inclusion complex with β-cyclodextrin [Drug. Develop. Ind. Pharm. 25 (1999) 1241].

In U.S. Pat. No. 5,849,329 the authors protected a process for preparing pharmaceutical compositions with controlled dissolution, prepared by grinding or dry-mixing active substances also with, inter alia, α-, β-, γ- and HP-β-cyclodextrins and their derivatives. As active substances there were cited naftazone, terfenadine, carbamazepine, glicazide, glibenclamide, bifonazole as well as nifedipine, diazepam and ketoprofen.

In U.S. Pat. No. 5,449,521 the authors protected pharmaceutical compositions containing griseofulvin, piroxicam, diacerein, diltiazem, megestrol acetate, nifedipine, nicergoline, ketoprofen, naproxen, diclofenac, ibuprofen, lorazepam, oxazepam as an active substance and, inter alia, cross-linked polymeric cyclodextrin. The cited pharmaceutical compositions were prepared by grinding the active substance and a suitable additive in mills saturated with the vapours of a solvent or of a mixture of solvents.

Besides, in U.S. Pat. No. 5,010,064 the authors protected an inclusion complex of dipyrimidole and β-cyclodextrin (molar ratio from 1:1 to 1:12), whereas in U.S. Pat. No. 5,019,563 a complex of ibuprofen sodium salt and β-cyclodextrin (molar ratio 1:0.2 to 1:0.75) was protected.

Further, in U.S. Pat. No. 5,674,854 the authors described and protected the preparation and an inclusion complex of pharmaceutically suitable salts of diclofenac and β-cyclodextrin (molar ratio 1:1) and in U.S. Pat. No. 5,744,165 the authors protected inclusion complexes of alkali metal salts and earth alkali metal salts of nimesulide with α-, β- and γ-cyclodextrins and derivatives thereof.

In the patent publication WO 93/00097 the authors claimed stable pharmaceutical preparations containing torasemide or its salts and additives such as hydroxy propylcellulose, polyvinylpyrrolidone, sodium-croscarmellose, cros-povidone, calcium-carboxymethylcellulose, lower substituted hydroxypropylcellulose, modified starch etc. Cyclodextrins were not cited therein.

In our further research in the field of torasemide we have suprisingly found that physical mixtures of modifications I–V of torasemide with cyclodextrins or cyclodextrin derivatives distinguish themselves by a faster dissolution of torasemide. Additionally, it has been suprisingly found that inclusion complexes of the modifications I–V of torasemide with cyclodextrins or cyclodextrin derivatives distinguish themselves by a faster dissolution of torasemide.

Firstly, the present invention relates to physiologically suitable physical mixtures of modifications I, II, III, IV or V of torasemide with cyclodextrins or cyclodextrin derivatives or to any mixture of modifications I, II, III, IV and V of torasemide and cyclodextrins or cyclodextrin derivatives.

Cyclodextrins contained in the physical mixtures are α-, β- and γ-cyclodextrins and their derivatives. Suitable derivatives of α-, β- and γ-cyclodextrins are their ethers and mixed ethers having one or more groups of anhydroglucose parts of cyclodextrin substituted with $C_{1-6}$alkyl, preferably methyl, ethyl or isopropyl; hydroxy$C_{1-6}$alkyl, preferably hydroxyethyl or hydroxypropyl or hydroxybutyl; carboxy$C_{1-6}$alkyl, preferably carboxymethyl or carboxyethyl; $C_{1-6}$alkylcarbonyl, preferably acetyl, $C_{1-6}$alkoxycarbonyl$C_{1-6}$alkyl or carboxy-$C_{1-6}$alkoxy-$C_{1-6}$alkyl, preferably carboxy-methoxypropyl or carboxyethoxypropyl; $C_{1-6}$alkoxycarbonyloxy$C_{1-6}$alkyl, preferably 2-acetyloxypropyl. Particularly important cyclodextrins or their derivatives are α-, β-and γ-cyclodextrins, 2-hydroxypropyl-α-cyclodextrin, 2-hydroxypropyl-β-cyclo-dextrin, 2-hydroxypropyl-γ-cyclodextrin, 2-hydroxyethyl-β-cyclodextrin, 2-hydroxy-ethyl-γ-cyclodextrin, 2,6-dimethyl-β-cyclodextrin and (2-carboxymethoxy)-propyl-β-cyclodextrin.

In general, in physical mixtures of the present invention the molar ratio of the modifications I–V of torasemide to cyclodextrins or cyclodextrin derivatives may range from 1:0.1 to 1:5.

Further, the present invention relates to a method for the preparation of the aforementioned physical mixtures of modifications I–V of torasemide and cyclodextrins or cyclodextrin derivatives. In practice, the method can be carried out according to the following method:

A modification I, II, III, IV or V of torasemide and cyclodextrins or cyclodextrin derivatives or any mixture of modifications I, II, III, IV and V of torasemide and cyclodextrins or cyclodextrin derivatives are combined in a specific molar ratio, homogenized in a mortar or mixers commonly used in pharmaceutical industry at a temperature and over a time period required for obtaining a mixture with the desired dissolution rate of torasemide.

In accordance with the first object of the invention, the present invention also relates to physiologically suitable inclusion complexes of modifications I, II, III, IV or V of torasemide with cyclodextrins or cyclodextrin derivatives or of any mixture of modifications I, II, III, IV and V of torasemide and cyclodextrins or cyclodextrin derivatives .

Cyclodextrins contained in inclusion complexes are α-, β- and γ-cyclodextrins or their derivatives. Suitable derivatives of α-, β- and γ-cyclodextrins are their ethers or mixed ethers having one or more groups of anhydroglucose parts of cyclodextrin substitued with $C_{1-6}$alkyl, preferably methyl, ethyl or isopropyl; hydroxy$C_{1-6}$alkyl, preferably hydroxyethyl or hydroxypropyl or hydroxybutyl; carboxy$C_{1-6}$alkyl, preferably carboxymethyl or carboxyethyl; $C_{1-6}$alkylcarbonyl, preferably acetyl; $C_{1-6}$alkoxy carbonyl $C_{1-6}$alkyl or carboxy-$C_{1-6}$alkoxy-$C_{1-6}$alkyl, preferably carboxymethoxypropyl or carboxyethoxypropyl; $C_{1-6}$alkoxycarbonyloxy$C_{1-6}$alkyl, preferably 2-acetyloxy-propyl. Particularly important cyclodextrins or their derivatives are α-, β- and γ-cyclodextrins, 2-hydroxypropyl-α-cyclodextrin, 2-hydroxypropyl-β-cyclodextrin, 2-hydroxypropyl-γ-cyclodextrin, 2-hydroxyethyl-β-cyclodextrin, 2-hydroxyethyl-γ-cyclodextrin, 2,6-dimethyl-β-cyclodextrin and (2-carboxymethoxy)propyl-β-cyclodextrin.

In general, in inclusion complexes of the present invention the molar ratio of modifications I–V of torasemide to cyclodextrins or cyclodextrin derivatives may range from 1:0 to 1:5.

Further, the present invention relates to a method for the preparation of the aforementioned inclusion complexes of modifications I–V of torasemide and cyclodextrins or cyclodextrin derivatives. In practice the method can be carried out according to the following method:

A modification I, II, III, IV or V of torasemide or any mixture of modifications I, II, III, IV and V of torasemide is added to an aqueous solution of cyclodextrins or cyclodextrin derivatives and, with or without the addition of an aqueous ammonia solution, it is stirred at a temperature and over a time period required for the formation of the inclusion complex. After the inclusion complex has been formed, water is removed by lyophilization, spray-drying, vacuum evaporation at lower temperatures or by any other method known in the pharmaceutical art.

The physical mixtures of modifications I–V of torasemide and cyclodextrins or cyclodextrin derivatives as well as the inclusion complexes of modifications I–V of torasemide and cyclodextrins or cyclodextrin derivatives prepared according to the methods of the present invention can, as a suitable torasemide form, be used as a diuretic or as an agent for preventing heart damages or heart tissue damages caused by metabolic or ionic abnormalities associated with ischemia, in the treatment of thrombosis, angina pectoris, asthma, hypertension, nephroedema, pulmonary edema, primary and secondary aldosteronism, Batter's syndrome, tumours, glaucoma, decrease of intraocular pressure, acute or chronic bronchitis, in the treatment of cerebral edema caused by trauma, ischemia, concussion of the brain, metastases or epileptic attacks and in the treatment of nasal infections caused by allergens.

The present invention also relates to pharmaceutical forms such as tablets, capsules, injections or sprays containing physical mixtures or inclusion complexes of modifications I, II, III, IV or V of torasemide and cyclodextrins or cyclodextrin derivatives or of any mixture of modifications I, II, III, IV and V of torasemide with cyclodextrins or cyclodextrin derivatives as the active ingredient, without any additives or in combination with one or more pharmaceutically acceptable additives such as sugar, starch, starch derivatives, cellulose, cellulose derivatives, mould release agents and antiadhesive agents and optionally agents for flowability regulation.

The present invention is illustrated but in no way limited by the following examples.

EXAMPLE 1

The modification I of torasemide according to PCT/WO 00/20395 (0.50 g) and an equimolar amount of β-cyclodextrin were homogenized in a mixer for 24 hours.

Figure 1:
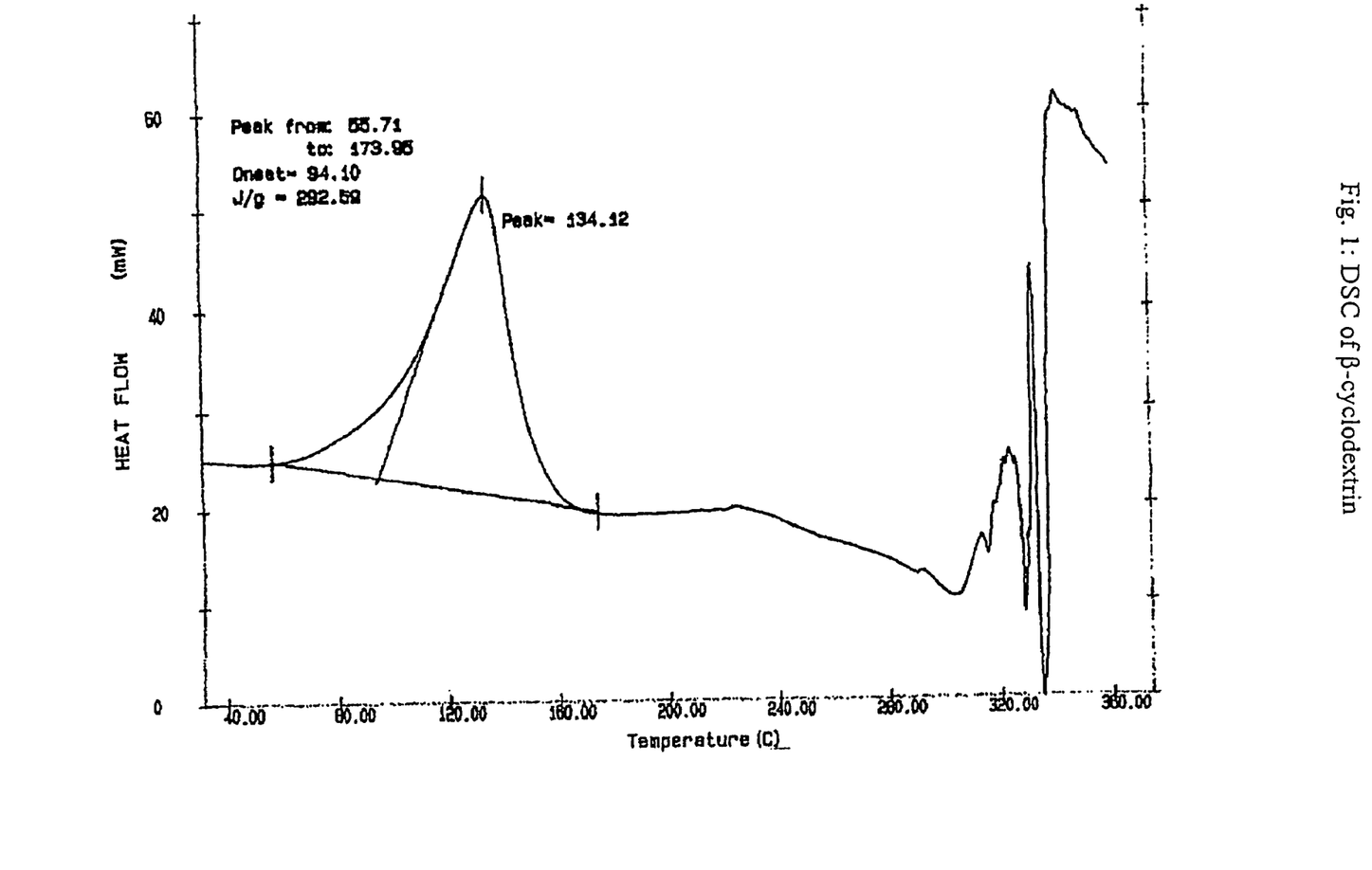
FIG. 1 represents the DSC curve of β-cyclodextrin.
Figure 2:
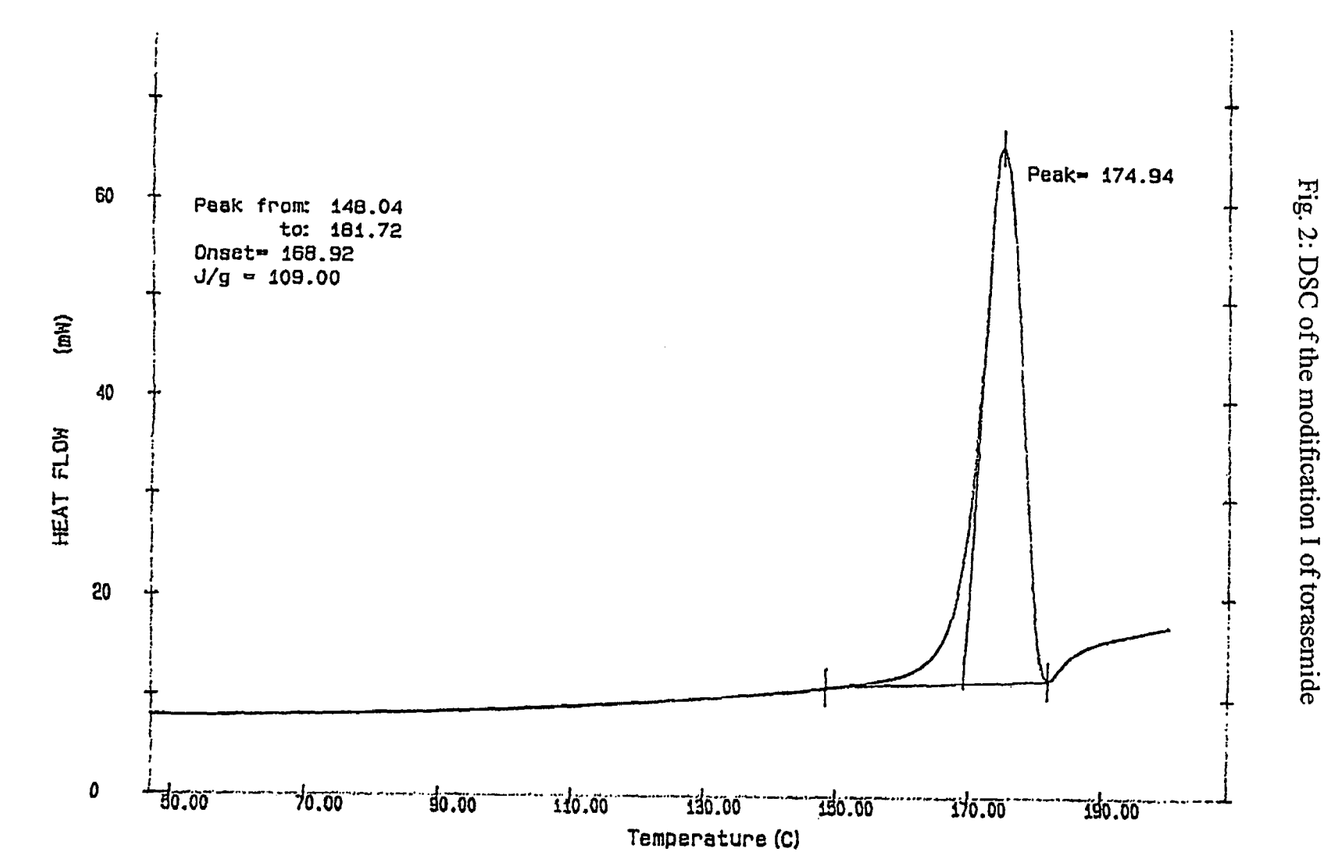
FIG. 2 represents the DSC curve of the modification I of torasermide.
Figure 3:
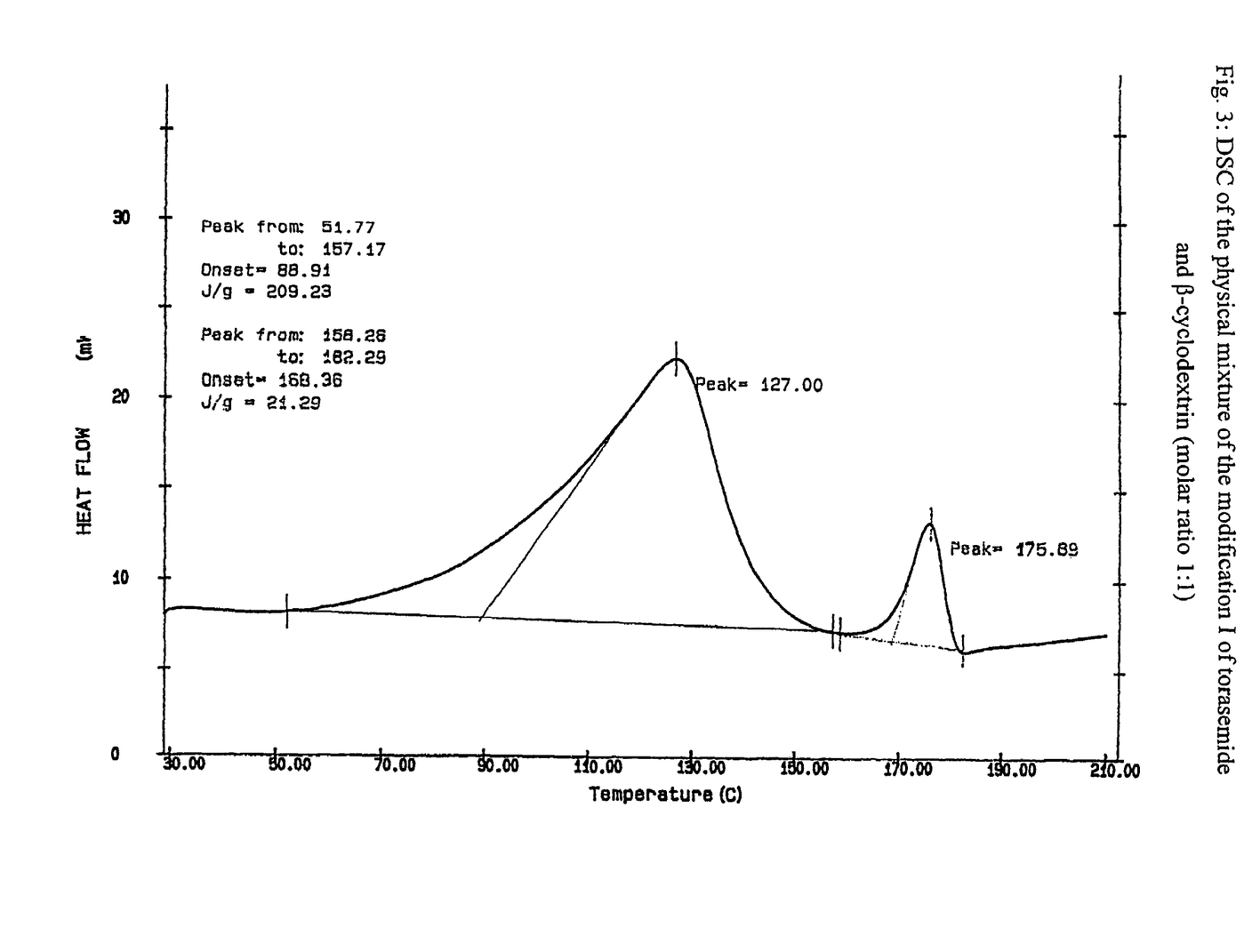
FIG. 3 represents the DSC curve of the physical mixture of the modification I of torasemide and β-cyclodextrin (molar ratio 1:1).

Differential scanning calorimetry (DSC) curve represented in FIG. 3 comprises exothermic peaks of the modification I of torasemide and β-cyclodextrin. The DSC analysis was performed on the apparatus Perkin-Elmer, model DSC7 at a heating rate of 25° C./min.

Figure 7:
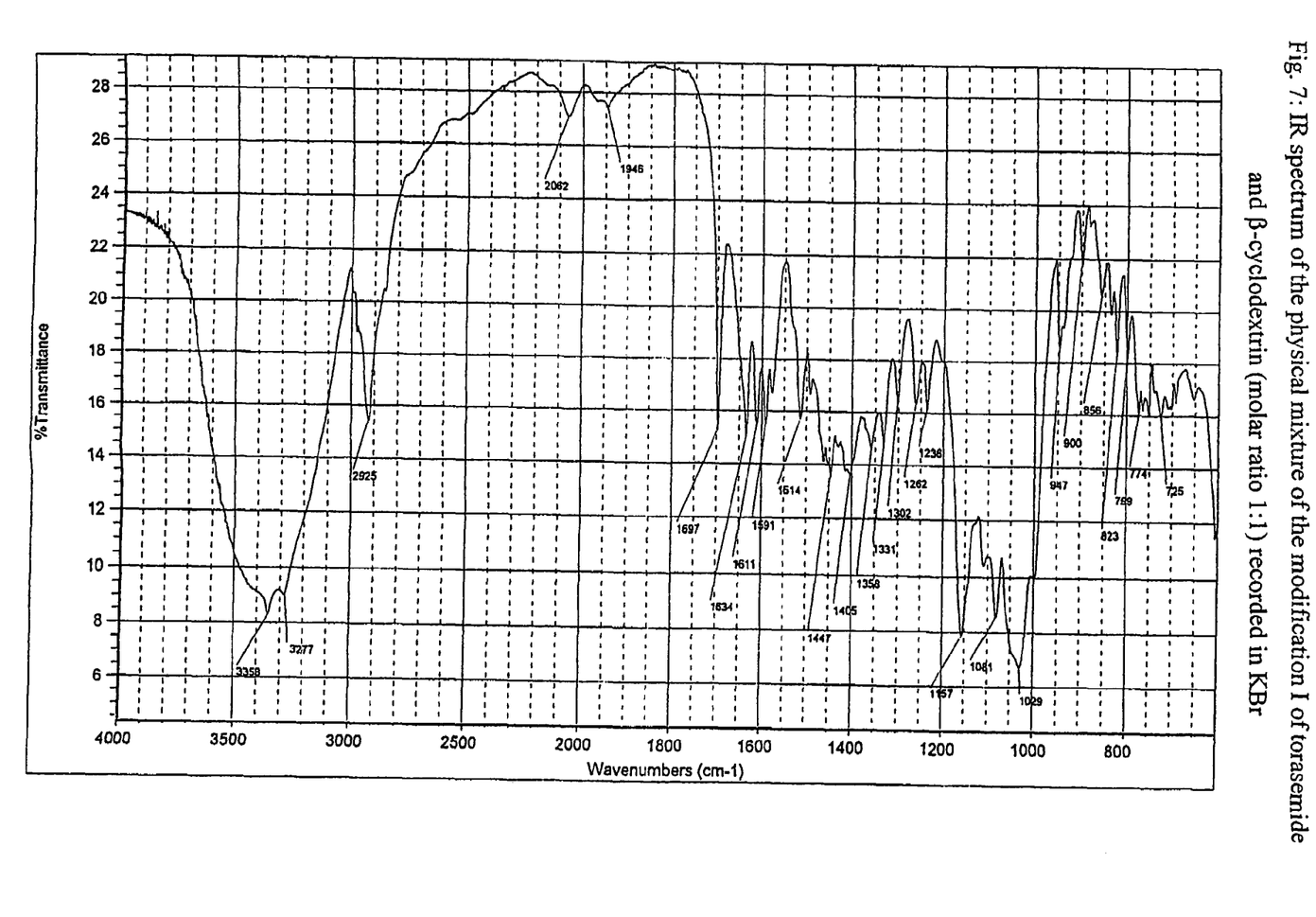
FIG. 7 represents the IR spectrum of the physical mixture of the modification I of torasemide and β-cyclodextrin (molar ratio 1:1) recorded in KBr.

The IR spectrum represented in FIG. 7 comprises characteristic peaks of the modification I of torasemide and β-cyclodextrin. The IR spectrum was recorded on the IR spectrophotometer Nicolet, model Magna 760 in the range from 4000 to 600 $cm^{-1}$.

Figure 11:
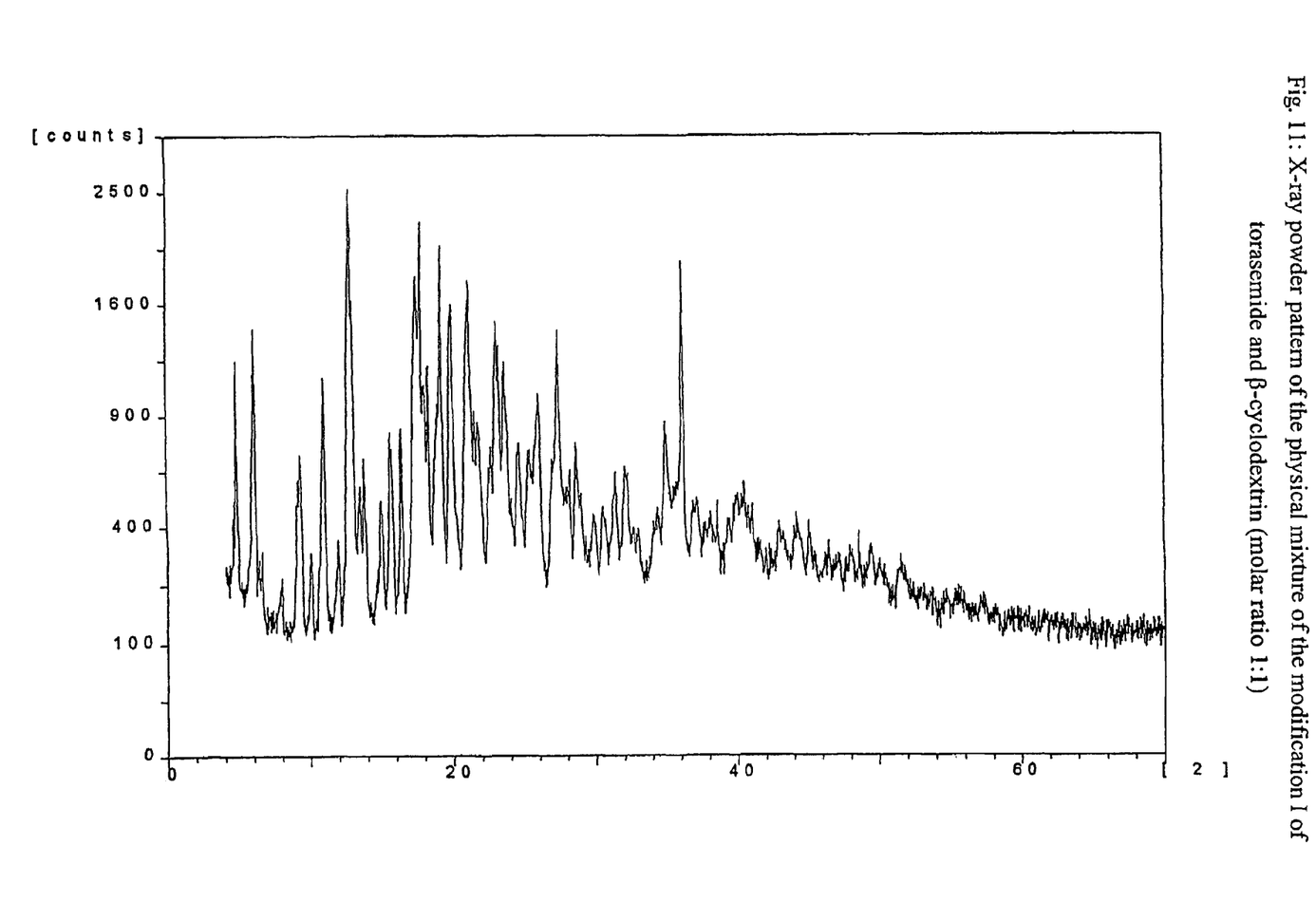
FIG. 11 represents the X-ray powder pattern of the physical mixture of the modification I of torasemide and β-cyclodextrin (molar ratio 1:1).

The representative X-ray powder pattern is represented in FIG. 11 and was recorded on the diffractometer PHILIPS, model PW 3710 in the range 2θ=5–40° using CuKα rays=1.541 Å. The recording step was 0.029° and the recording time was 1 s per step.

EXAMPLE 2

The physical mixture of the modification I of torasemide and β-cyclodextrin prepared according to the Example 1 of the present invention was subjected to testing the release of the active substance in water at the temperature of 37° C. (USP 24) and the results are shown in Table 1.

TABLE 1

Release of torasemide from the physical mixture of the modification I of torasemide and β-cyclodextrin (molar ratio 1:1) in water (USP 24) (37° C., 50 rpm, 1000 ml)

| Time | Released torasemide (%) | |
|---|---|---|
| (min) | Modification I of torasemide | Physical mixture |
| 0 | 0 | 0 |
| 15 | 0.7 | 32.2 |
| 30 | 20.3 | 57.1 |

TABLE 1-continued

Release of torasemide from the physical mixture of the modification I of torasemide and β-cyclodextrin (molar ratio 1:1) in water (USP 24) (37° C., 50 rpm, 1000 ml)

| Time | Released torasemide (%) | |
|---|---|---|
| (min) | Modification I of torasemide | Physical mixture |
| 45 | 38.5 | 70.2 |
| 60 | 51.8 | 80.6 |
| 90 | 68.5 | 89.1 |
| 120 | 78.7 | 93.8 |

EXAMPLE 3

β-Cyclodextrin (1.81 g) was dissolved in 50 ml of demineralised water and 10 drops of an aqueous ammonia solution were added. Subsequently, an equimolar amount of the modification I of torasemide prepared according to PCT/WO 00/20395 was added to the solution, it was vigorously stirred for 24 hours and then filtered and water was removed by lyophilization.

The formation of the inclusion complex of torasemide and β-cyclodextrin was proven by the data obtained by differential scanning calorimetry, IR analysis and X-ray powder pattern.

Figure 4:
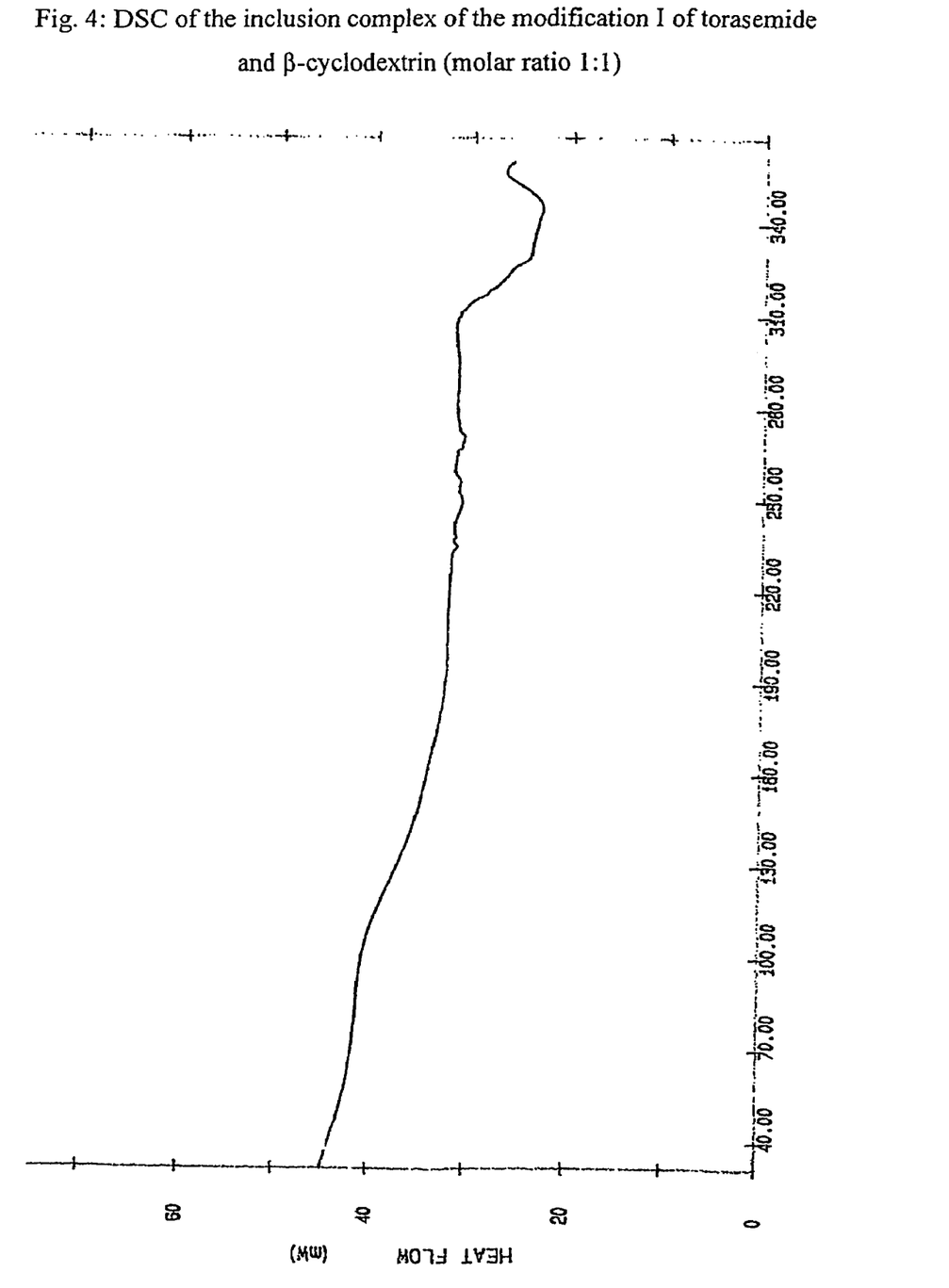
FIG. 4 represents the DSC curve of the inclusion complex of the modification I of torasemide and β-cyclodextrin (molar ratio 1:1).

The differential scanning calorimetry (DSC) curve represented in FIG. 4 does not comprise strong peaks characteristic of the modification I of torasemide and of ,β-cyclodextrin.

Figure 5:
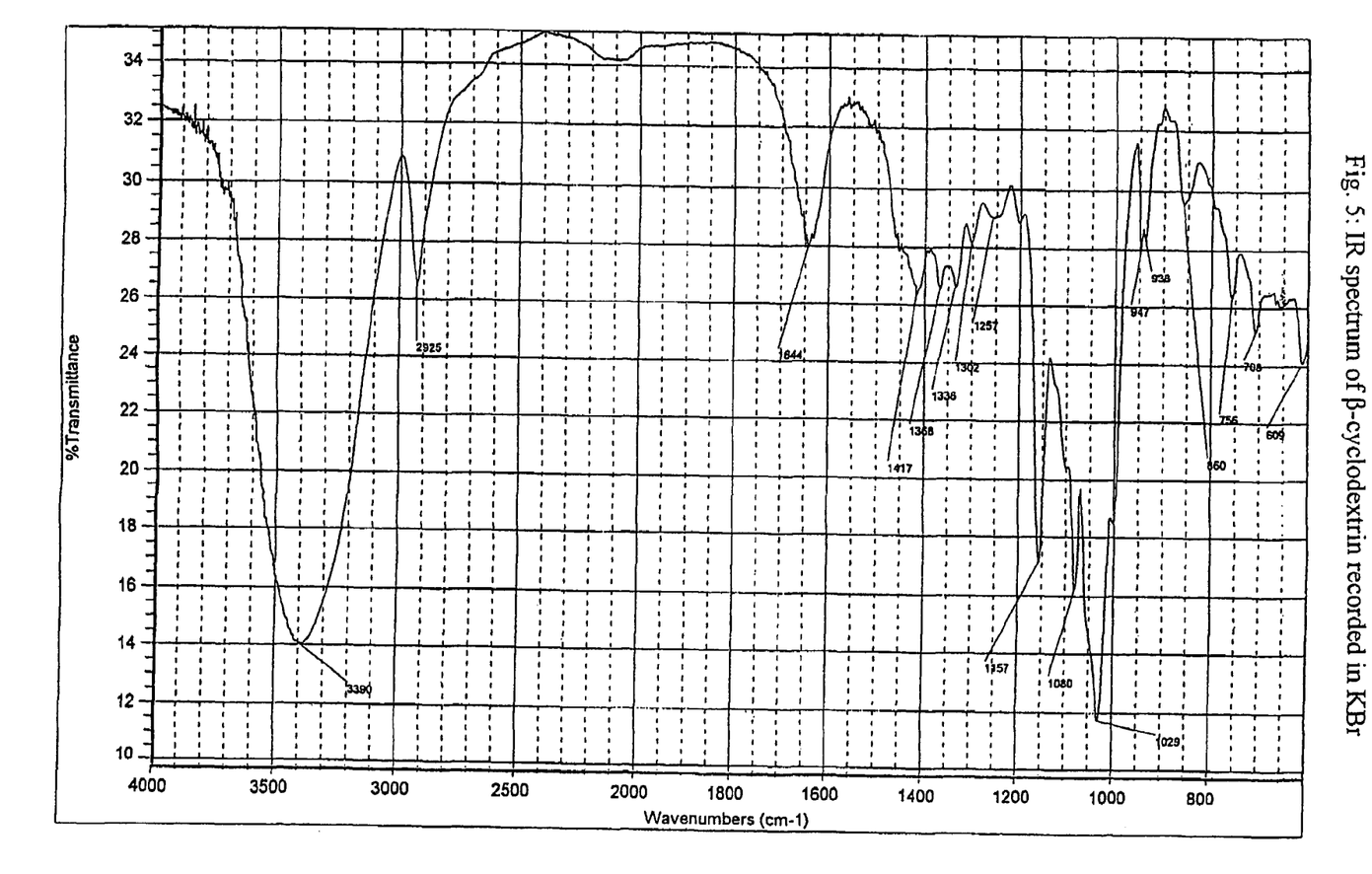
FIG. 5 represents the IR spectrum of β-cyclodextrin recorded in KBr.
Figure 6:
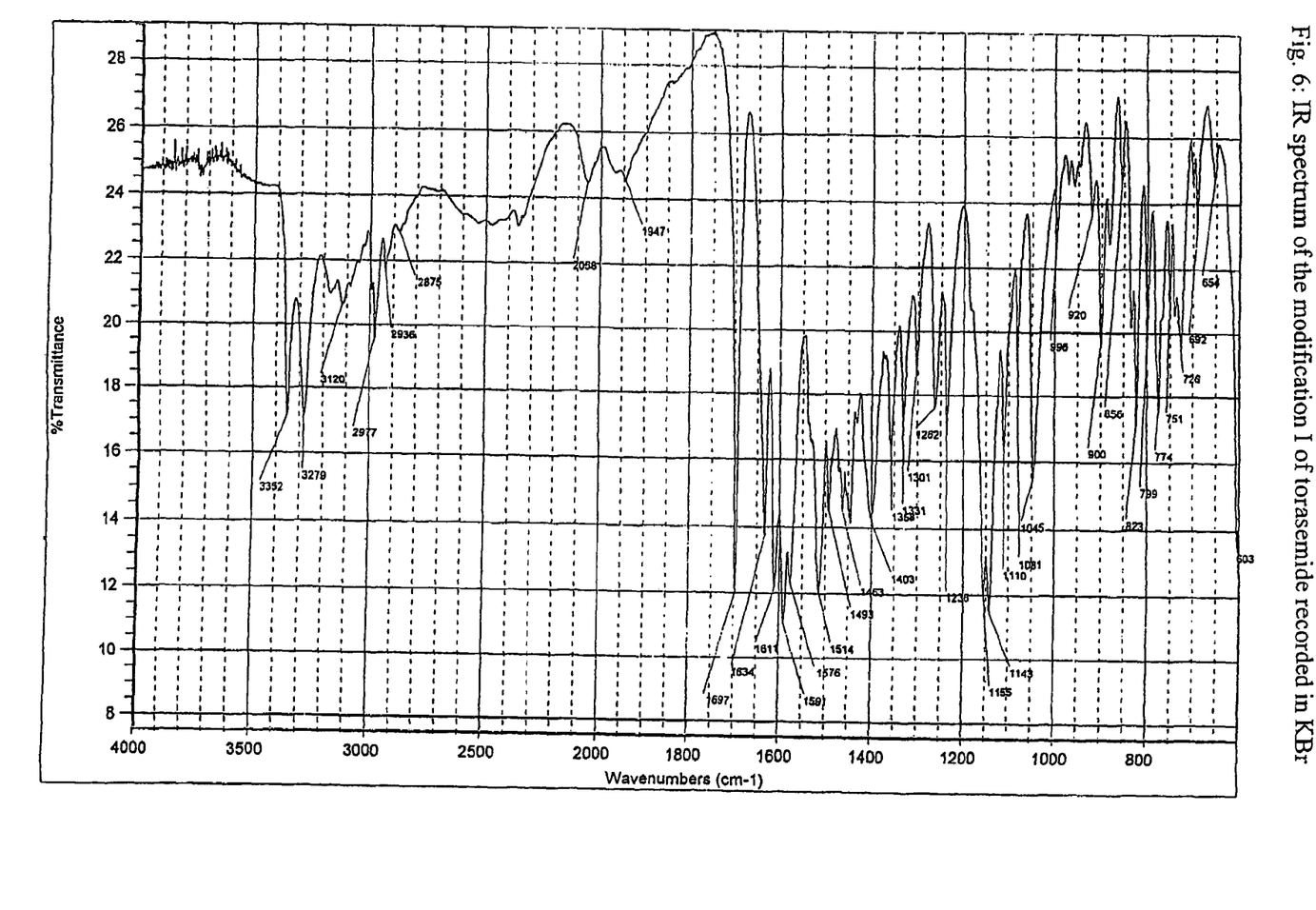
FIG. 6 represents the IR spectrum of the modification I of torasemide recorded in KBr.
Figure 8:
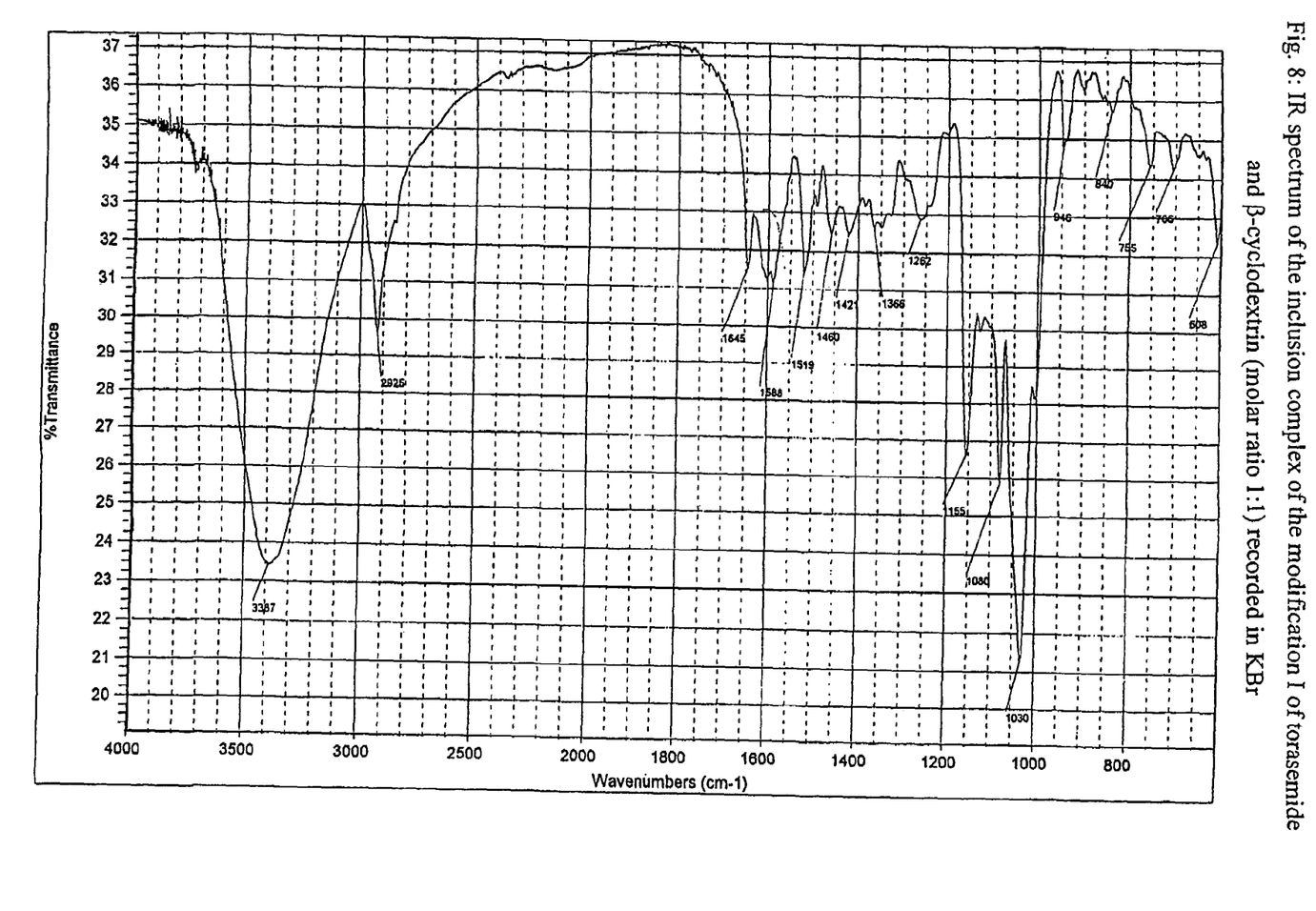
FIG. 8 represents the IR spectrum of the inclusion complex of the modification I of torasemide and β-cyclodextrin (molar ratio 1:1) recorded in KBr.
Figure 9:
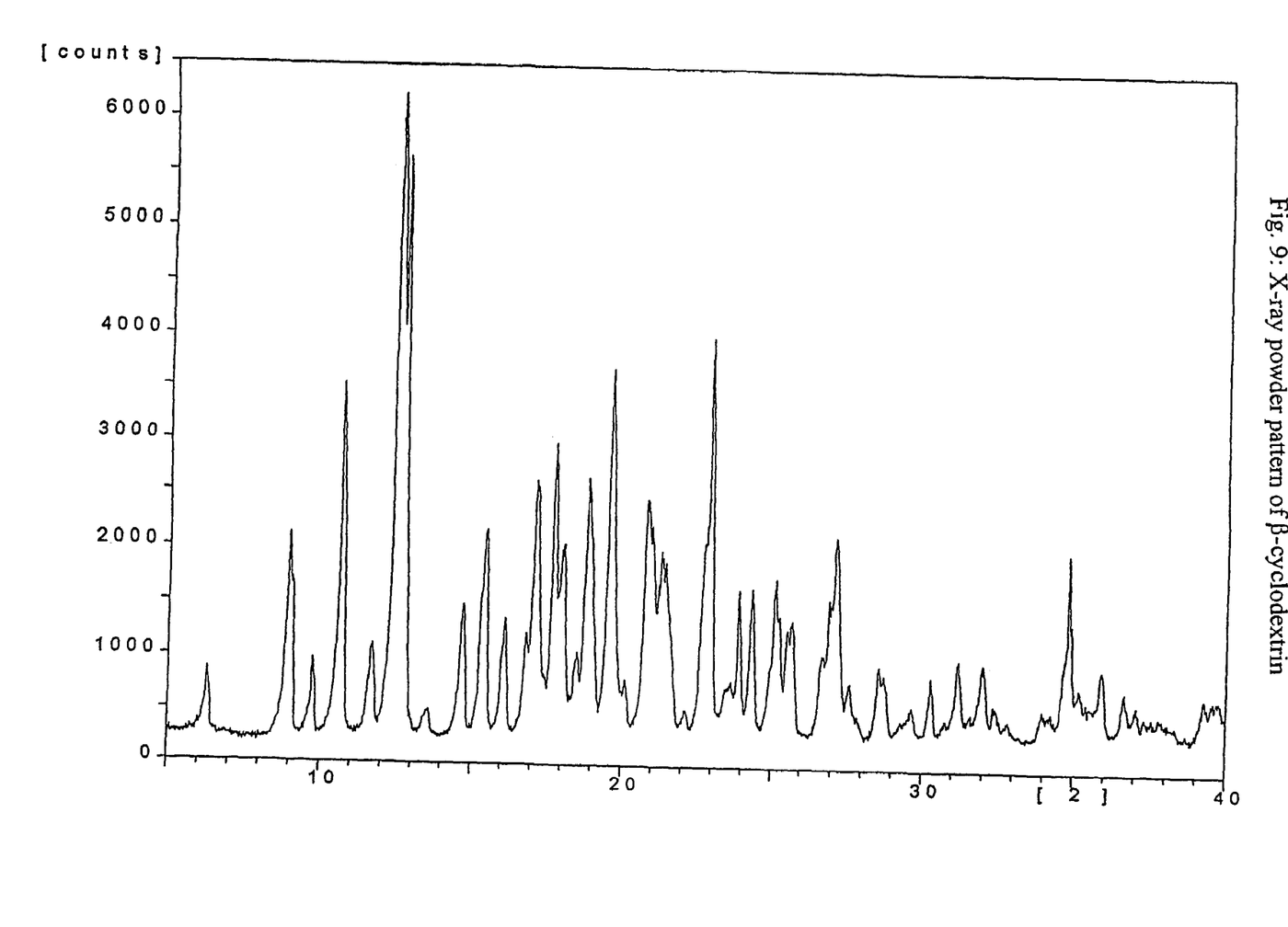
FIG. 9 represents the X-ray powder pattern of β-cyclodextrin.

The IR spectrum represented in FIG. 8 strongly differs from the IR spectrum of the modification I of torasemide and from the IR spectrum of β-cyclodextrin represented in FIGS. 5 and 6.

Figure 10:
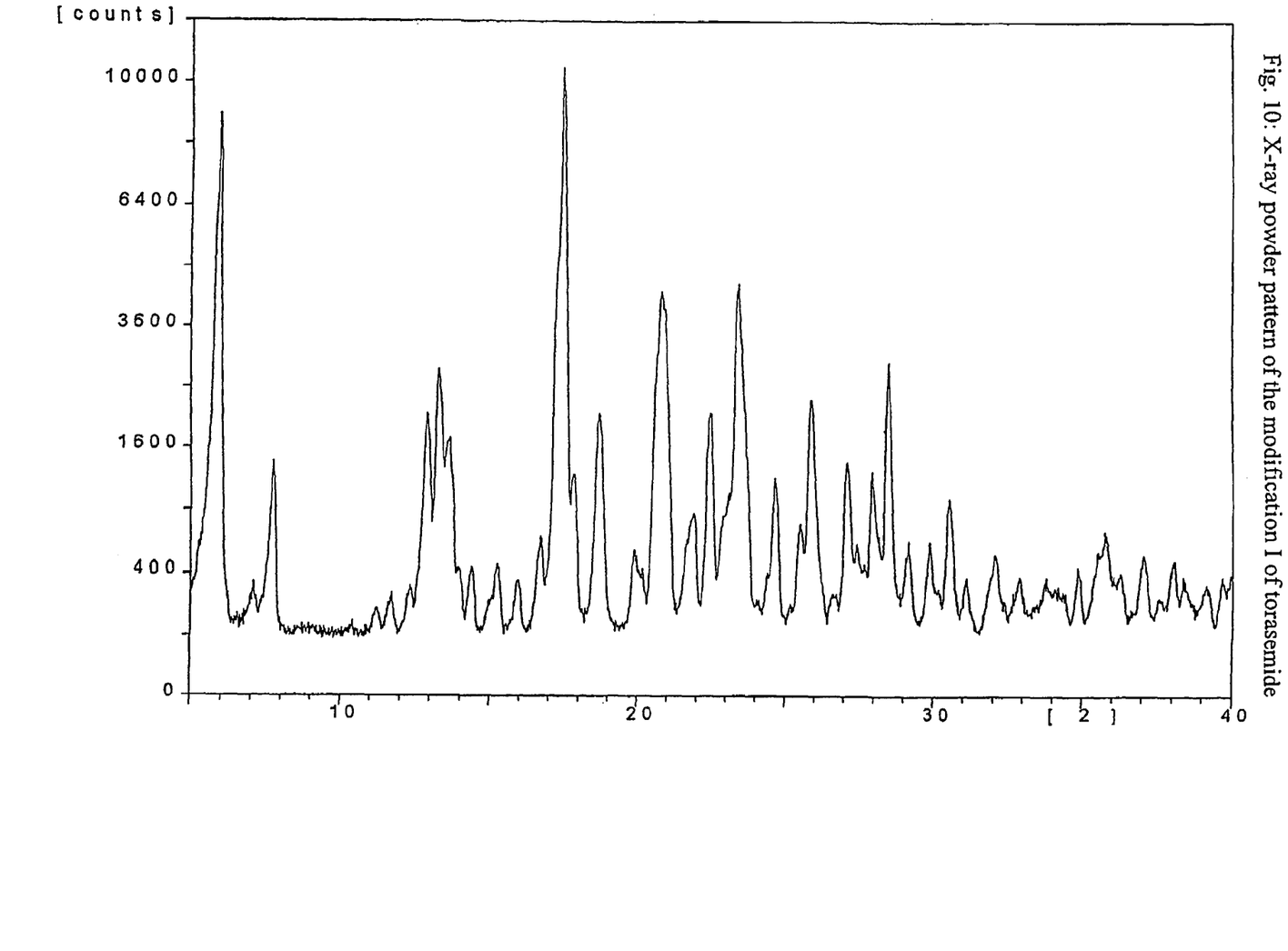
FIG. 10 represents the X-ray powder pattern of the modification I of torasemide.
Figure 12:
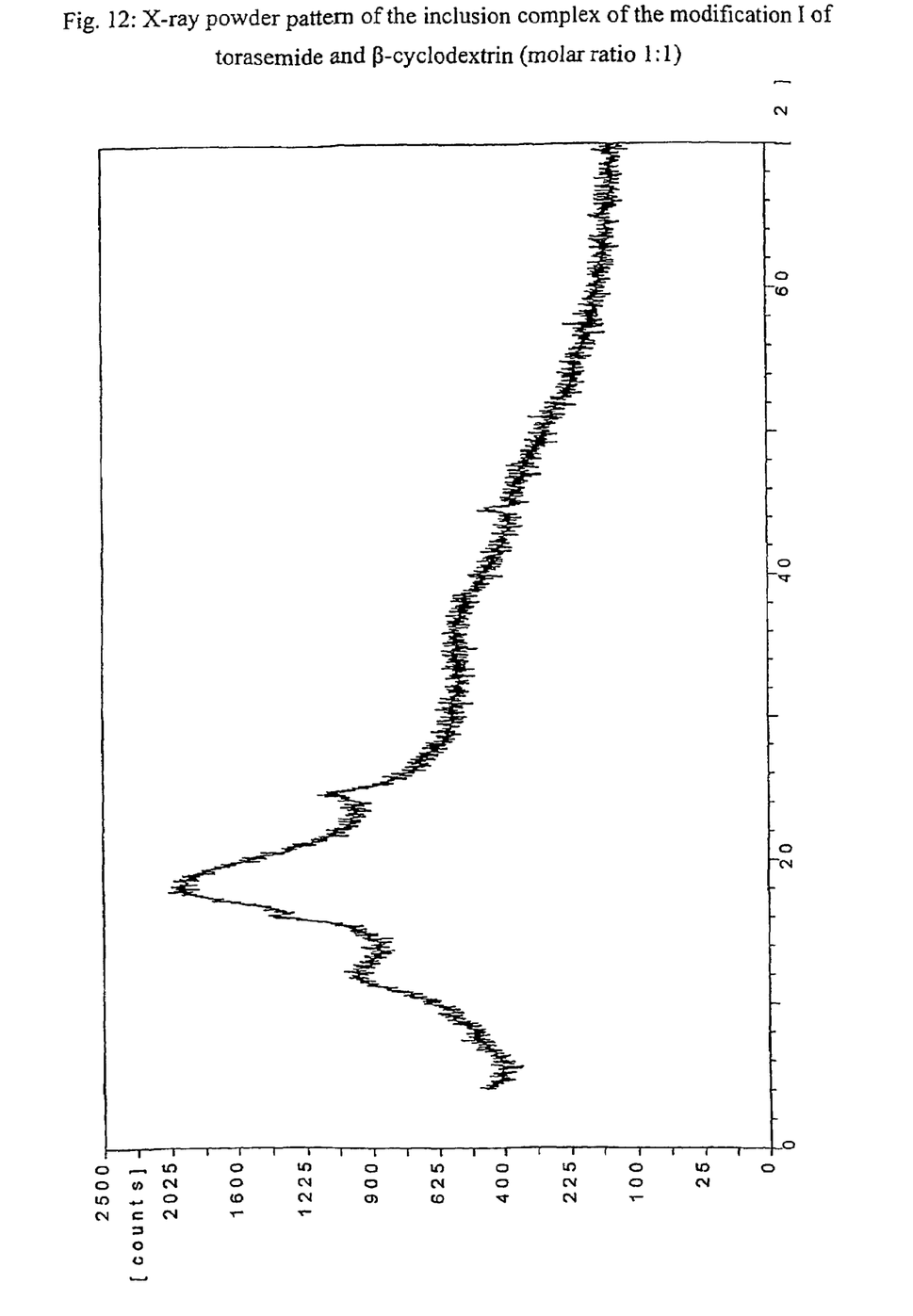
FIG. 12 represents the X-ray powder pattern of the inclusion complex of the modification I of torasemide and β-cyclodextrin (molar ratio 1:1).

The X-ray powder pattern represented in FIG. 12 strongly differs from the X-ray powder pattern of the modification I of torasemide and the X-ray powder pattern of β-cyclodextrin represented in FIGS. 10 and 11.

EXAMPLE 4

β-Cyclodextrin (0.28 g) was dissolved in 50 ml of demineralised water, the solution was heated to 80° C. under vigorous stirring, it was stirred for 60 minutes and then an equimolar amount of the modification I of torasemide prepared according to PCT/WO 00/20395 was added over 90 minutes. Subsequently, the hot solution was filtered, cooled to room temperature, whereupon water was removed by lyophilization.

The IR spectrum of the thus obtained sample was identical to the IR spectrum of the sample prepared according to the Example 3 of the present invention.

EXAMPLE 5

The inclusion complex of the modification I of torasemide and β-cyclodextrin to the Example 3 of the present invention was subjected to testing the release of the active substance in water at the temperature of 37° C. (USP 24) and the results are shown in Table 2.

TABLE 2

Release of torasemide from the inclusion complex of the modification I of torasemide and β-cyclodextrin (molar ratio 1:1) in water (USP 24) (37° C., 50 rpm, 1000 ml)

| Time | Released torasemide (%) | |
|---|---|---|
| (min) | Modification I of torasemide | Inclusion complex |
| 0 | 0 | 0 |
| 15 | 0.7 | 95.8 |
| 30 | 20.3 | 98.2 |
| 45 | 38.5 | 97.9 |
| 60 | 51.8 | 98.3 |
| 90 | 68.5 | 98.8 |
| 120 | 78.7 | 98.5 |

The invention claimed is:

1. An inclusion complex which comprises torasemide and a member selected from the group consisting of cyclodextrin and cyclodextrin derivative.

2. An inclusion complex according to claim 1, wherein cyclodextrin is selected from a group consisting of α-cyclodextrin, β-cyclodextrin and γ-cyclodextrin.

3. An inclusion complex according to claim 1, wherein the cyclodextrin derivative is selected from the group of ethers or mixed ethers of α-cyclodextrin, β-cyclodextrin, and γ-cyclodextrins having one or more groups of anhydroglucose parts of cyclodextrin substituted with a member selected from the group consisting of $C_{1-6}$-alkyl, hydroxy$C_{1-6}$alkyl, carboxy$C_{1-6}$alkyl, $C_{1-6}$alkylcarbonyl, $C_{1-6}$alkoxycarbonyl$C_{1-6}$alkyl or carboxy-$C_{1-6}$alkoxy-$C_{1-6}$alkyl, and $C_{1-6}$alkoxycarbonyloxy-$C_{1-6}$alkyl.

4. An inclusion complex according to claim 1, wherein the cyclodextrin derivative is selected from the group consisting of 2-hydroxypropyl-α-cyclodextrin, 2-hydroxypropyl-β-cyclodextrin, 2-hydroxypropyl-γ-cyclodextrin, 2-hydroxyethyl-β-cyclodextrin, 2-hydroxyethyl-γ-cyclodextrin, 2,6-dimethyl-β-cyclodextrin and (2-carboxymethoxy)-propyl-β-cyclodextrin.

5. An inclusion complex according to claim 1 wherein the torasemide and cyclodextrin or cyclodextrin derivative are in a molar ratio from 1:0.1 to 1:5.

6. A method for the preparation of an inclusion complex according to claim 1, which method comprises reacting torasemide and cyclodextrin or cyclodextrin derivative in water with or without an aqueous solution of a base.

7. The method for the preparation of an inclusion complex according to claim 6, which comprises using as the aqueous solution of a base, an aqueous ammonia solution.

8. The method for the preparation of an inclusion complex according to claim 6, which is carried out at temperatures from 10° C. to 100° C.

9. The method for the preparation of an inclusion complex according to claim 6, which is carried out for from 0.1 hours to 7 days.

10. The method for the preparation of an inclusion complex according to claim 6, which further comprises after formation of the said inclusion complex, removing the water and the base by drying.

11. The method for the preparation of an inclusion complex according to claim 10, wherein the said drying is carried out by lyophilization, spray-drying, vacuum evaporation or vacuum drying.

12. A method for treating a patient in need of a diuretic, an agent for inhibiting heart damages or heart tissue damages caused by metabolic or ionic abnormalities associated with ischemia, treatment of thrombosis, agnia pectoris, asthma, hypertension, nephro edema, pulmonary edema, primary and secondary aldosteronism, Batter's syndrome, tumours, glaucoma, decrease of intraocular pressure, acute or chronic bronchitis, treatment of cerebral edema caused by trauma, ischemia, concussion of the brain, metastases or epileptic attacks or treatment of nasal infections caused by allergens which comprises administering to said patient an effective amount of an inclusion complex according to claim 1.

13. A pharmaceutical composition which comprises an inclusion complex according to claim 1 as the active ingredient in combination with one or more pharmaceutically acceptable additives.

14. A pharmaceutical form according to claim 13, being a tablet a capsule, an injection or a spray.

15. An inclusion complex according to claim 1 wherein the cyclodextrin derivative is selected from the group consisting of ethers or mixed ethers of $\alpha$-, $\beta$- and $\gamma$-cyclodextrins having one or more groups of anhydroglucose parts of cyclodextrin substituted with a member selected from the group consisting of methyl, ethyl, isopropyl, hydroxyethyl, hydroxypropyl, hydroxybutyl, carboxymethyl, carboxyethyl, acetyl, carboxymethoxypropyl, carboxyethoxypropyl and 2-acetyloxypropyl.

* * * * *